United States Patent [19]
Pologe et al.

[11] Patent Number: 5,766,127
[45] Date of Patent: Jun. 16, 1998

[54] METHOD AND APPARATUS FOR IMPROVED PHOTOPLETHYSMOGRAPHIC PERFUSION-INDEX MONITORING

[75] Inventors: Jonas A. Pologe; Robert M. Tobin, Jr., both of Boulder, Colo.

[73] Assignee: Ohmeda Inc., Liberty Corner, N.J.

[21] Appl. No.: 722,705

[22] Filed: Sep. 30, 1996

Related U.S. Application Data

[60] Provisional application No. 60/015,448, Apr. 15, 1996.

[51] Int. Cl.$^6$ ............................................. A61B 5/00
[52] U.S. Cl. ........................... 600/310; 600/473; 600/476; 600/504
[58] Field of Search .................... 128/633, 664–667, 128/691, 687–690; 600/310, 473, 475, 476, 477, 500–504

[56] References Cited

U.S. PATENT DOCUMENTS

| | | | |
|---|---|---|---|
| 4,109,643 | 8/1978 | Bond et al. | 128/666 |
| 4,167,331 | 9/1979 | Nielson | 128/633 |
| 4,867,165 | 9/1989 | Noller et al. | 128/666 |
| 4,869,253 | 9/1989 | Craig, Jr. et al. | 128/664 |
| 5,203,342 | 4/1993 | Sakai . | |
| 5,386,827 | 2/1995 | Chance et al. | 128/664 |
| 5,503,148 | 4/1996 | Pologe et al. | 128/633 |

*Primary Examiner*—Jennifer Bahr
*Assistant Examiner*—Bryan K. Yarnell
*Attorney, Agent, or Firm*—William A. Schoneman; Salvatore P. Pace

[57] ABSTRACT

An improved method and apparatus for the monitoring perfusion of the tissue of a patient by arterial blood is provided. An optical path length change is calculated for a number of digitized samples of a received light intensity signal generated by a photo detector that receives light directed into a patient's tissue by one or more light emitting diodes or laser diodes. The optical path length changes are summed over a predetermined time such as one half cardiac cycle or other set interval to generate a perfusion index. An average perfusion index value may also be generated. In calculating the perfusion index spectral content compensation may be employed to compensate for the variety of center wavelengths associated with the spectral contents of various emitters.

23 Claims, 5 Drawing Sheets

METHOD AND APPARATUS FOR IMPROVED PHOTOPLETHYSMOGRAPHIC PERFUSION-INDEX MONITORING

CROSS-REFERENCE TO RELATED APPLICATION

This application is based on a provisional application filed on Apr. 15, 1996 and granted Ser. No. 60/015,448.

BACKGROUND OF THE INVENTION

The present invention concerns generally monitoring the perfusion of tissue under test resulting from the flow of arterial blood and more particularly concerns accurately monitoring the perfusion of this tissue substantially independently of the degree of oxygenation of the blood by means of optical radiation transmitted through the tissue.

During surgery and other medical procedures, clinicians find it useful to be able to determine the degree of perfusion of tissue resulting from arterial blood flow in the patient. In measurements of oxygen saturation made by pulse oximetry, the quality of the measurements is directly proportional to the strength of the physiological signal at the probe site. In fact all pulse oximeters have a threshold of perfusion below which they are unable to provide accurate readings or may cease to operate. The strength of the physiological signal is determined by the degree of perfusion of the arterial blood at the probe site. Thus a measure of the degree of perfusion at the probe site is useful in determining the quality of the readings made by a pulse oximeter.

Measurement of the perfusion of particular tissue portions such as membranes of the bowel permits necrotic tissue to be distinguished from viable tissue in procedures for surgically resectioning diseased or injured tissue. See, for example, Y. Katz and G. Shoshani, *Journal of Pediatric Surgery* Volume 27, pages 509–510 (April 1992) and J. A. Salo et al.,*The American Journal of Surgery*, Volume 163, pages 446–447 (April 1992).

Measurement of the perfusion in the fingers of the hand while the ulnar and radial arteries in the arm supplying the hand are occluded one at a time permits the collateral circulation to the hand to be evaluated. Determination of collateral blood flow to the hand from the ulnar artery is useful in determining whether the radial artery may be cannulated during major surgery without depriving the hand of sufficient oxygenated blood.

U.S. Pat. No. 4,867,165 to Noller et al. discloses a method for estimating perfusion in a body member which involved passing light through the body member. One of the methods disclosed in the Noller '165 patent involved passing light of two different wavelengths through a member of the body and measuring the variation in intensity of light emerging from the body member due to arterial blood volume variation. The patent discloses that a perfusion thickness $\Delta d$, or overall cross-sectional enlargement, was proportional to the expression $\Delta I/I_{max}$. $\Delta I$ is defined in FIG. 4 of the Noller '165 patent as the largest peak-to-valley variation in current signal produced by a photo receiver irradiated by light influenced by the pulsation of the arterial blood. The term $I_{max}$ is defined by FIG. 4 to be the maximum overall current signal detected. The '165 patent discloses formulas for obtaining a relative thickness variation $\Delta d/d$ of the body member or a relative volume variation $\Delta V/V$, where d corresponded to an overall thickness of the body member and V corresponded to a measurement volume between a light source and the detector.

Although the method of the Noller et al. '165 patent provides an estimate of perfusion, the method is subject to errors and inaccuracies on a number of points. For example, the greater the peak-to-valley current signal variation $\Delta I$ for a given maximum signal $I_{max}$, the greater the error in the approximation cited in support of the assertion that the overall cross-sectional enlargement $\Delta d$ was proportional to $\Delta I/I_{max}$. In addition, on a beat-to-beat basis, the determination of both $\Delta I$ and $\Delta I/I_{max}$ are expected to be subject to noise and interference, which could introduce error into the resulting estimate of perfusion. Furthermore, a relative variation in thickness $\Delta d/d$ normalized to the thickness d of a body member as determined by the method of the Noller and Forstner '165 patent would in general not be comparable for body members of significantly different sizes or composed of different tissue types. Similarly, a relative variation in volume $\Delta V/V$ normalized to a measurement volume V of a body member as determined by the method of the patent would not be comparable in general for different body members. In addition, because one use of the perfusion index is to indicate the strength of the signal available to the photoplethysmographic device, it is important not to normalize in a way that would diminish the value of this important information. Finally, the need for a value for thickness or volume of the body member under test requires either the use of an unvalidated estimate or an extra measurement and some method for entering this estimate into the monitoring instrument.

Pulse-oximeter instruments have been commercially available for measuring the degree of oxygen saturation in arterial blood by means of time-varying absorption of light by tissue supplied with pulsating arterial blood with a technique known generally as photoplethysmography. Conventional pulse oximeter instruments transmit light at two different center wavelengths through tissue. The spectral characteristics of oxygenated hemoglobin and reduced hemoglobin in arterial blood differ for the two different light signals emitted by the pulse oximeter instrument. Since the arterial blood pulsates, the light transmitted through the tissue generally exhibits a time-varying component, as well as a time-invariant component. From a ratio formed by dividing a ratio of the time-varying component to the time-invariant component of the light intensity at one center wavelength transmitted through the tissue by the ratio of the time-varying component to the timeinvariant component of the transmitted intensity at the second center wavelength, the degree of oxygen saturation in the arterial blood can be determined. See, for example, an article by the present inventor in *International Anesthesiology Clinics*, Volume 25, pp. 137–153 (1987), the contents of which are hereby incorporated by reference.

One commercial pulse-oximeter instrument, the Ohmeda Biox 3700 Oximeter commercially available from Ohmeda Corporation of Boulder, Colorado, includes a display of the percent modulation of the transmitted-light signal from one of the two light signals emitted by the instrument which is caused by pulsation of the arterial blood through which the light signal is transmitted. Although the percent modulation can provide a rough indication of the degree of perfusion in the tissue under test by arterial blood, the extent of modulation in the 3700 oximeter depends to some extent on the level of oxygen saturation of the blood, as well as on the degree of perfusion. Consequently, the percent modulation information has limited utility as a qualitative indication of the actual degree of perfusion.

Internally, the Ohmeda Biox 3700 Oximeter computed a sampling-interval incremental value termed a "pulsatility index," which served to measure an incremental change in the effective optical path through the tissue under test over a sampling interval which was a small fraction of a single cardiac pulse. The sampling-interval pulsatility index was employed internally in the instrument as an element of a weighting procedure for determining the reliability of the oxygen saturation measurement. The sampling-interval pulsatility index of the Ohmeda Biox 3700 Oximeter did not provide information concerning the perfusion over a cardiac pulse cycle or half cycle.

BRIEF SUMMARY OF THE INVENTION

This application discloses a photoplethysmographic method for the continuous realtime measurement of the perfusion of tissue by arterial blood, which can provide a high degree of accuracy and is substantially independent of the extent of oxygen saturation of the blood and which avoids problems of the prior art noted above.

The method of the invention measures the perfusion of the tissue under test as it is supplied with pulsating arterial blood.

One method according to the present invention comprises the step of generating at least approximately monochromatic light having a first spectral content denoted $\lambda_1$, generated by a first emitter, and directing the light into a portion of the tissue under test in order to pass through the tissue portion along a first effective optical path. The method further comprises generating at least approximately monochromatic light having a second spectral content denoted $\lambda_2$, generated by a second emitter, significantly different from $\lambda_1$, and directing the radiation into a portion of the tissue under test to pass through the tissue portion along substantially the same optical path.

The method of the invention further comprises the use of means for detecting the received light transmitted from the tissue such as a photodiode or other appropriate detector. $I_{\lambda_1}$, and $I_{\lambda_2}$ are the output light received from tissue after absorption and modulation by the various absorbers in the tissue under test and the arterial blood.

The method of the invention also comprises sampling and digitizing the received light $I_{\lambda_1}$, at a sequence of sampling times {tj} to produce a sequence of digital values, $\{I_{\lambda_1}(tj)\}$. The sampling rate is appreciably faster than the heart rate of the patient. In conventional pulse oximetry sampling rates of 30Hz or faster have been typical.

Similarly $I_{\lambda_2}$ is digitized at the same sample times generating an analogous sequence of digital values, $\{I_{\lambda_2}(tj)\}$.

For each sampling time in the sequence of sampling times {tj}, and for each emitter we calculate a normalized change in intensity:

$$\frac{\Delta I_\lambda(t_j)}{I_\lambda(t_j)} \equiv \frac{I_\lambda(t_j) - I_\lambda(t_{j-1})}{[I_\lambda(t_j) - I_\lambda(t_{j-1})]/2}$$

Then the optical path length change $\Delta L(tj)$ in the tissue over any given sample interval, $t_{j-1}$ to $t_j$, can be calculated as follows:

$$\Delta L(t_j) = K \left[ (E_{\lambda_2}^R - E_{\lambda_2}^O) \frac{\Delta I_{\lambda_1}(t_j)}{I_{\lambda_1}(t_j)} - (E_{\lambda_1}^R - E_{\lambda_1}^O) \frac{\Delta I_{\lambda_2}(t_j)}{I_{\lambda_2}(t_j)} \right],$$

where $E_{\lambda_1}^R$ is an effective extinction coefficient of reduced hemoglobin at $\lambda_1$, $E_{\lambda_1}^O$ is the effective extinction coefficient of oxygenated hemoglobin at $\lambda_1$, where $E_{\lambda_2}^R$ is the effective extinction coefficient of reduced hemoglobin at $\lambda_2$, $E_{\lambda_2}^R$ is the effective extinction coefficient of oxygenated hemoglobin at $\lambda_2$, and K is a predetermined proportionality constant.

The effective extinction coefficients should be selected based on the spectral contents of the emitters being used. One method for achieving this is to have a table containing the effective extinction coefficients for a number of various spectral contents. Information on the actual spectral content of the emitter being used is transferred from a sensor to the oximeter for selection of the proper effective extinction coefficients for the emitter from the stored table.

The method of the invention also comprises summing the values $\Delta L(tj)$ corresponding to a plurality of contiguous sampling times tj which fall within a diastolic-to-systolic transition time interval or within a systolic-to-diastolic transition time interval to obtain a pulsatility value (or perfusion index) measuring the perfusion of the tissue under test by the arterial blood. Therefore the Perfusion Index is defined as:

$$PI \equiv \sum_{j=\text{Systole}}^{\text{diastole}} \Delta L(t_j) \quad \text{Or} \quad PI \equiv \sum_{j=\text{Diastole}}^{\text{Systole}} \Delta L(t_j)$$

Finally, the method of the invention further comprises displaying the perfusion index pulsatility value to a user. The Perfusion Index value is equivalent to the effective change in optical path length in the tissue under test from systole to diastole (or from diastole to systole) which can be calculated and displayed on a beat by beat basis.

Preferably, in the method for measuring perfusion of the invention the proportionality constant K equals:

$$K = [[Hb](E_{\lambda_1}{}^O E_{\lambda_2}{}^{R-E}{}_{\lambda_1}{}^R E_{\lambda_2}{}^O)]^{-1}$$

Where [Hb] is the total hemoglobin concentration in the arterial blood. This constant K then makes the perfusion index at least approximately constitute an effective-optical path length change in units of physical length.

Given the equations expressed above it is obviously necessary to identify diastole and systole in a photoplethysmographic waveform. There exists many published methods for identifying the peak (diastole) and valley (systole) of a photoplethysmographic waveform the most straight forward being simple peak detection. There is however an alternate method preferred for calculation of perfusion index. The technique consists of the following steps. For a predetermined window of time, typically 2 seconds, all the $\Delta L$s are recorded. A simple peak (and valley) detection scheme is used on that window of data. Finally the $\Delta L$s are summed from the first of the two (peak or valley) to be detected to the other to compute the perfusion index. The advantage of this method is that it provides a perfusion index on any data, in the last two seconds of data collected, whether or not there was even a pulse present in the tissue under test. For example if the patient had a blood pressure cuff on the iplsilateral arm leading to a finger sensor being used for perfusion index measurement the sensor would cease to read any variations due to arterial pulsation when the cuff was inflated above systolic pressure. This technique for perfusion index would show the clinician a value of zero (or of the level of noise artifact) under these conditions, or any other that interrupts blood flow, indicating some loss of blood flow to the tissue under test.

BRIEF DESCRIPTION OF THE DRAWINGS

Preferred embodiments of the invention are described below with reference to the following drawings.

DETAILED DESCRIPTION OF THE INVENTION

Figure 1:
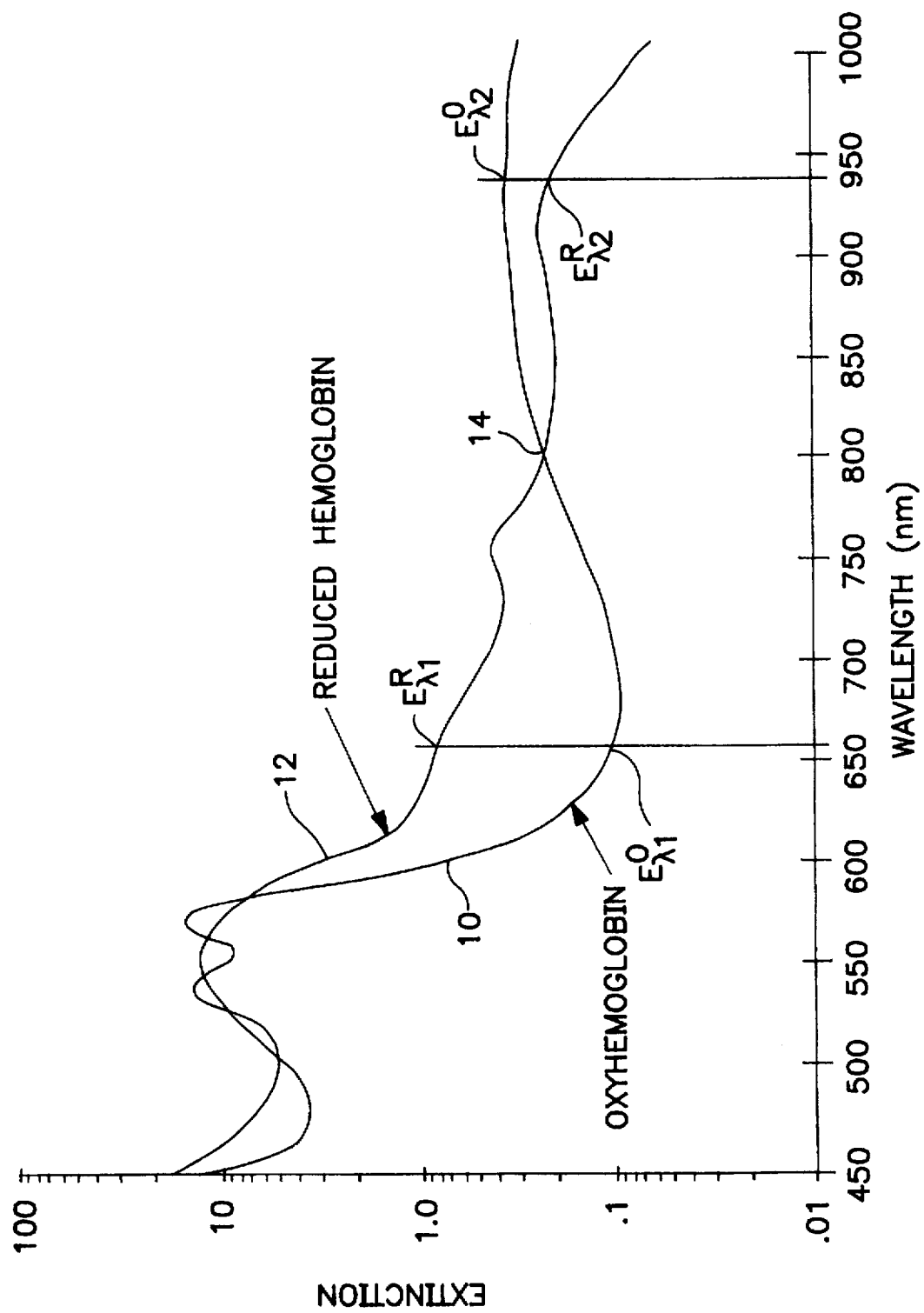
FIG. 1 is a graph of the extinction curves of oxyhemoglobin and reduced hemoglobin. The spectra are shown in terms of millimolarextinction, on a logarithmic scale, versus wavelength in nanometers.

The perfusion index monitor of the present invention measures the total change in effective optical path length of arterial blood as it pulsates into or out of the tissue under test on a beat-by-beat basis. The maximal change in effective optical path length corresponds to the change in path length from diastole to systole in the cardiac pulse cycle, or, equivalently, from systole to diastole. The perfusion index monitor is a photoplethysmographic device, generally similar to a conventional pulse oximeter. Preferably, the photoplethysmographic device of the invention includes an emitter capable of emitting optical radiation with a unique spectral content and directing the radiation into the tissue under test. In preferred photoplethysmographic devices of the invention, the optical radiation emitter includes two light-emitting diodes having distinctly different center wavelengths and spectral contents.

In a photoplethysmographic system of the invention, the intensity of optical radiation transmitted through the tissue under test is sampled frequently in comparison with the rate of change in the optical path length through the absorbers, which in the case of this invention, are oxygenated and reduced hemoglobin in arterial blood in the tissue. Serial measurements of the intensity of the transmitted light are made. Further, essentially simultaneous measurements are made for the intensity of the light from each of the two emitters (or channels) after the light passes through the tissue under test. The measurements of intensity can be represented as: $I_{\lambda 1}(t_j)$, $I_{\lambda 2}(t_j)$ where $I_{\lambda 1}(t_j)$ and $I_{\lambda 2}(t_j)$ are the intensity measurements from a first and second emitter respectively at times $\{t_j\}$.

The differential absorption, $dA\lambda$, of the light for each emitter for any two adjacent samples in a preferred embodiment of the invention may be approximated as:

$$dA_{\lambda_1} \approx \Delta A_{\lambda_1} = \frac{[I_{\lambda_1}(t_j) - I_{\lambda_1}(t_{j-1})]}{[I_{\lambda_1}(t_j) + I_{\lambda_1}(t_{j-1})]/2}$$

and $$dA_{\lambda_2} \approx \Delta A_{\lambda_2} = \frac{[I_{\lambda_2}(t_j) - I_{\lambda_2}(t_{j-1})]}{[I_{\lambda_2}(t_j) + I_{\lambda_2}(t_{j-1})]/2}$$

As is understood from the basic science of pulse oximetry, the differential absorption at wavelength $\lambda$ is also approximately equal to:

$$\Delta A_\lambda = E_\lambda^O C^O \Delta L^O + E_\lambda^R C^R \Delta L^R$$

Where C is the concentration of the specific absorber. For each emitter in a two emitter system we have:

$$\Delta A_{\lambda 1} = E_{\lambda 1}^O C^O \Delta L^O + E_{\lambda 1}^R C^R \Delta L^R$$

and $$\Delta A_{\lambda 2} = E_{\lambda 2}^O C^O \Delta L^O + E_{\lambda 2}^R C^R \Delta L^R$$

Various models may be used to understand the operation of a preferred embodiment of the photoplethysmographic perfusion-index monitor of the present invention. Consider first a compartmentalized model for a body member under test.

In the compartmentalized model, it is assumed that light passing through the body member under test passes first through all the tissue, then all the bone, then the venous blood, then the arterial oxyhemoglobin, and then the arterial reduced hemoglobin. In this model, the concentration of the oxyhemoglobin and the reduced hemoglobin are taken to be equal and the path lengths of the two components $\Delta L^R$ and $\Delta L^O$ vary as the blood pulsates into and out of the tissue under test. Further the ratio of the path lengths of these two components will change as the oxygen saturation of the tissue under test changes. The hemoglobin concentrations are assumed to be fixed and equal for $C^O$ and $C^R$ and equal to the total hemoglobin concentration of the arterial blood. Thus, the last two equations above can be rewritten as follows, assuming each extinction coefficient is multiplied by a hemoglobin concentration constant:

$$\Delta A^{\lambda 1} = C [E_{\lambda 1}^O \Delta L^O + E_{\lambda 1}^R \Delta^R], \text{ and } \Delta A_{\lambda 2} = C [E_{\lambda 2}^O \Delta L^O + E_{\lambda 2}^R \Delta L^R].$$

Reviewing these last two equations, the extinction coefficients are all constants, and the differential absorption terms $\Delta A$ can be measured by the photoplethysmographic device. Therefore, the only unknowns in the two equations are the two optical path-length increments $\Delta L^O$ and $\Delta L^R$, terms which can be solved for with straightforward algebra. Then, assuming that the only two absorbers in the blood are the oxygenated and reduced hemoglobin, the change in effective optical path length over any two samples in time can be defined as a sampling-interval "pulsatility value:" $\Delta P_j = \Delta L^R + \Delta L^O$. Summing the pulsatility values from diastole to systole (or vice versa) and taking the absolute value of this sum provides an excellent approximation to the total change in effective optical path length on a beat-by-beat basis, which defines an overall pulsatility value or "perfusion index" denoted PI.

$$PI = \left| \sum_{\text{Diastole}}^{\text{Systole}} (\Delta L^R + \Delta L^O) \right|.$$

The preferred perfusion index thus defined provides a quantitative estimate of the perfusion of the tissue under test by the arterial blood substantially independent of the degree of oxygen saturation of the blood.

The perfusion index will ordinarily vary in magnitude to some extent from beat to beat and therefore it will generally be preferable to smooth the values over time.

One method for determining a perfusion index is to identify the peak and the valley of each pulse in a normal photoplethysmographic waveform. The sampling-interval pulsatility value would be calculated for each data point from the peak to the valley and these values summed to generate the perfusion index. Since the falling edge of the photoplethysmographic waveform is equivalent to the rising edge of the arterial pressure waveform, there is no dicrotic notch on the falling edge of the waveform. Summing each sampling-interval pulsatility value from the peak to the valley, which corresponds to the rising edge of a pressure waveform, yields the perfusion index for the given pulse.

The perfusion index is useful in providing real-time information as to the change in arterial path length through which light passes with arterial pulsation. The perfusion index may also provide the information that arterial pulsation does not exist at all when that is the case. The procedure set forth above may be modified to determine a perfusion index even in cases of low perfusion. In particular, searching for an adjacent peak and valley alone in a photoplethysmographic waveform might not to be practical for applications in which there may be little or no perfusion. Instead, the photoplethysmographic waveform may be examined in a time window of suitable predetermined duration. A time window of two seconds in duration is preferred for many applications. The photoplethysmographic perfusion-index monitor could evaluate the individual data points collected over the course of the time window. In the case of a perfusion-index monitor which samples photoplethysmographic data at intervals of approximately 1/30th of a second, a two-second window would provide 61 data points independent of the cardiac pulse rate or amplitude. The highest point and the lowest point in the last two-seconds of data would then be identified. The sampling-interval pulsatility value would then be calculated for each data point from the highest to lowest point in the two-second window, or the lowest to highest, depending on which point was first in time. The resulting sampling-interval pulsatility values would be signed values. These pulsatility values would then be summed from the highest to the lowest (or lowest to highest) value in the two-second window to yield a perfusion index. Preferably, this calculation would be repeated every approximately one second for display and/or output.

The windowing procedure described above will function even when there is no arterial pulsation at the site of the tissue under test. There will be one point in the last two-second epic of data which has a maximum value and one point which has a minimum value, even if the two points for the index are identical. In the case of identical maximum and minimum values, the calculation for perfusion index would be zero.

As a practical matter, there are other considerations that should preferably be taken into account in determining the perfusion index.

The first such consideration is that photoplethysmographic arterial-pulsation signals tend to ride on top of a respiratory artifact. As this respiratory artifact is primarily venous in nature and does not indicate arterial pulsation, it is preferable to remove the artifact to the largest extent possible from the calculation for perfusion index. The effect of the respiratory artifact will, in most cases, be fairly small. However, the artifact may be essentially eliminated in a straightforward manner, as described below. The respiratory artifact can be removed by applying a high-pass digital filter to the digitized time-varying data with a cut-off frequency set to pass the arterial-pressure waveform and filter out the respiratory artifact.

Although an approximately two-second window ordinarily spans a full cardiac cycle waveform of 30 beats per minute, a full cardiac cycle generally is not required to determine a perfusion index. To determine a perfusion index, a peak and a valley must be found contiguous within the window. Consequently, slightly more than one complete half-cycle, either from a peak to a valley, or from a valley to a peak, should be spanned by the window.

In the calculation of a perfusion index, the differential absorption dA values should be represented accurately. The differential absorption dA values should be calculated as the incremental change in intensity over the sampling interval - preferably 1/30th of a second - divided by an absolute intensity base value in that sampling interval. A preferred representation for the absolute intensity base value is an average between the respective absolute intensities at the end points of sampling interval.

In cases where a receiver gain or a light-emitting-diode drive level has changed in the course of a perfusion index determination, data from sample windows may be distorted. The perfusion-index monitor should preferably not proceed with the calculation over the sample period if there has been a change in receiver gain or in an emitter drive-level which occurred over that sample period. Note that settling times after gain or drive level changes should be accounted for as well. For example, if a filter response causes the photoplethysmographic data to misrepresent the photoplethysmographic signal for some settling-time period after a gain change, then there should be a delay for determining the next perfusion index until the settling time has been accounted for.

DETAILED DESCRIPTION OF PREFERRED EMBODIMENT

Turning now to FIG. 1, the extinction curve for oxygenated hemoglobin 10 and reduced hemoglobin 12 are shown. The vertical axis of the spectra gives the millimolar extinction coefficients on a logarithmic scale. The horizontal axis gives the wavelength of the radiation in nanometers.

As may be seen from the spectra of FIG. 1, oxygenated hemoglobin and reduced hemoglobin have generally distinct spectra with respect to optical light radiation. In other words, the extinction coefficients of oxygenated and reduced hemoglobin differ for all wavelengths of optical radiation except for a few so-called "isobestic" wavelengths - such as point 14 - at which the spectra cross one another.

Figure 2:
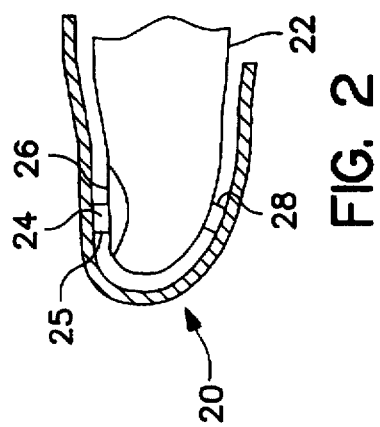
FIG. 2 is a schematic side view, partially cut away, of a photoplethysmographic sensor mounted on a figure tip of a patient.

Turning now to FIG. 2, a photoplethysmographic sensor 20 is affixed to a finger tip 22 of a patient. The sensor 20 includes a red-light light-emitting-diode 24 and an infrared-light light-emitting diode 25 (not shown). The two light-emitting diodes 24, 25 are positioned on a surface of the sensor 20 adjacent to a finger nail 26 of the finger tip 22. Each of the light-emitting-diodes 24, 25 is oriented to project light emitted by the diode through the finger nail 26 into the finger tip 22 of the patient.

The red-light light-emitting-diode 24 emits substantially monochromatic (or at least narrow band) light with a center wavelength of about 660 nm, which is in the red region of the optical-radiation spectrum. The infrared-light light-emitting-diode 25 emits substantially monochromatic light with a wavelength centered at about 940 nm, which lies in the near-infrared region of the optical radiation spectrum.

Attached to a surface of the photoplethysmographic sensor 20 at a location adjacent to a surface of the finger tip 22 generally opposing the finger nail 26 and the light-emitting-diodes 24, 25 is a silicon photodiode 28. The silicon photodiode 28 is adapted to detect light emitted by both the red- and infrared-light light-emitting-diodes 24, 25 of the photoplethysmographic sensor 20.

The two light-emitting-diodes 24, 25 are positioned in close proximity to one another on the surface of the photoplethysmographic sensor 20. Preferably, the two light-emitting-diodes 24, 25 are less than one millimeter apart. The close proximity of the two light-emitting-diodes 24, 25 ensures that the optical paths extending from the respective light-emitting-diodes 24, 25 to the silicon photodiode 28 are essentially the same.

The photoplethysmographic sensor 20 is a conventional device used with pulse-oximeter instruments, and includes wiring for connecting the two light-emitting-diodes 24, 25 to switched drive-current sources (not shown) in the perfusion index monitor and for connecting the photodiode 28 to the monitor for processing transmitted-radiation-intensity signals generated by the photodiode 28 in response to radiation emitted by the light-emitting-diodes 24 and passing through the finger tip 22 of the patient and falling upon the photodiode 28.

Turning again to FIG. 1, the center wavelengths of the light emitted by the red-and infrared-light light-emitting-diodes 24, 25 - namely, 660 nm and 940 nm, respectively -are indicated on the spectra. It may be seen that the extinction coefficient of oxygenated hemoglobin for light of a wavelength of at about 660 nm, denoted $E_{\lambda 1}{}^O$ in FIG. 1, is roughly on order of magnitude less than the extinction coefficient for reduced hemoglobin for light of a wavelength of about 660 nm, which is denoted $E_{\lambda 1}{}^R$ in FIG. 1. Conversely, for light of a wavelength of about 940 nm the extinction coefficient of oxygenated hemoglobin, denoted $E_{\lambda 2}{}^O$, is significantly greater than the extinction coefficient of reduced hemoglobin for that wavelength, denoted $E_{\lambda 2}{}^R$.

Figure 3B:
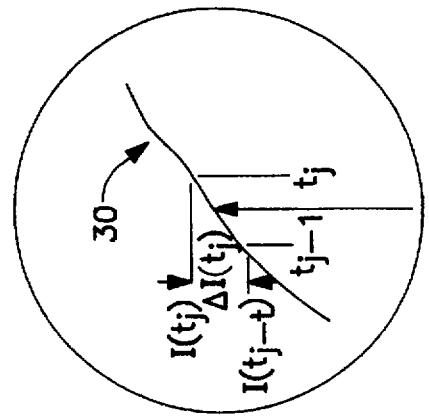
FIG. 3 is a schematic graph of the intensity of light transmitted through a finger tip as a function of time. The graph of FIG. 3 includes an expanded-scale inset to show representative sampling times $t_{j-1}$, $t_j$ and corresponding transmitted intensity values $I(t_{j-1})$ and $I(t_j)$, together with the intensity increment $\Delta I(t_j)$ and the intensity base value $[I(t_j)+I(t_{j-1})]/2$.
Figure 3A:
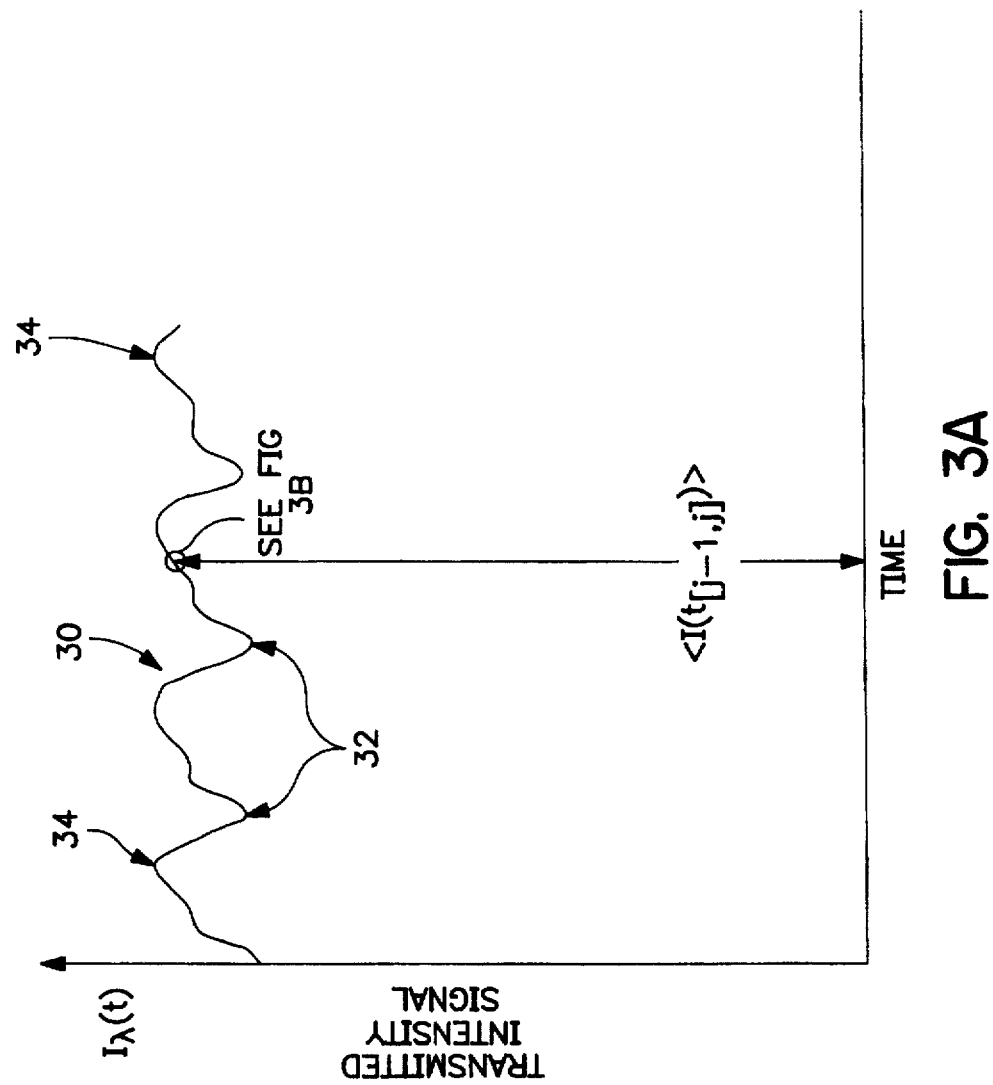
Figure 4:
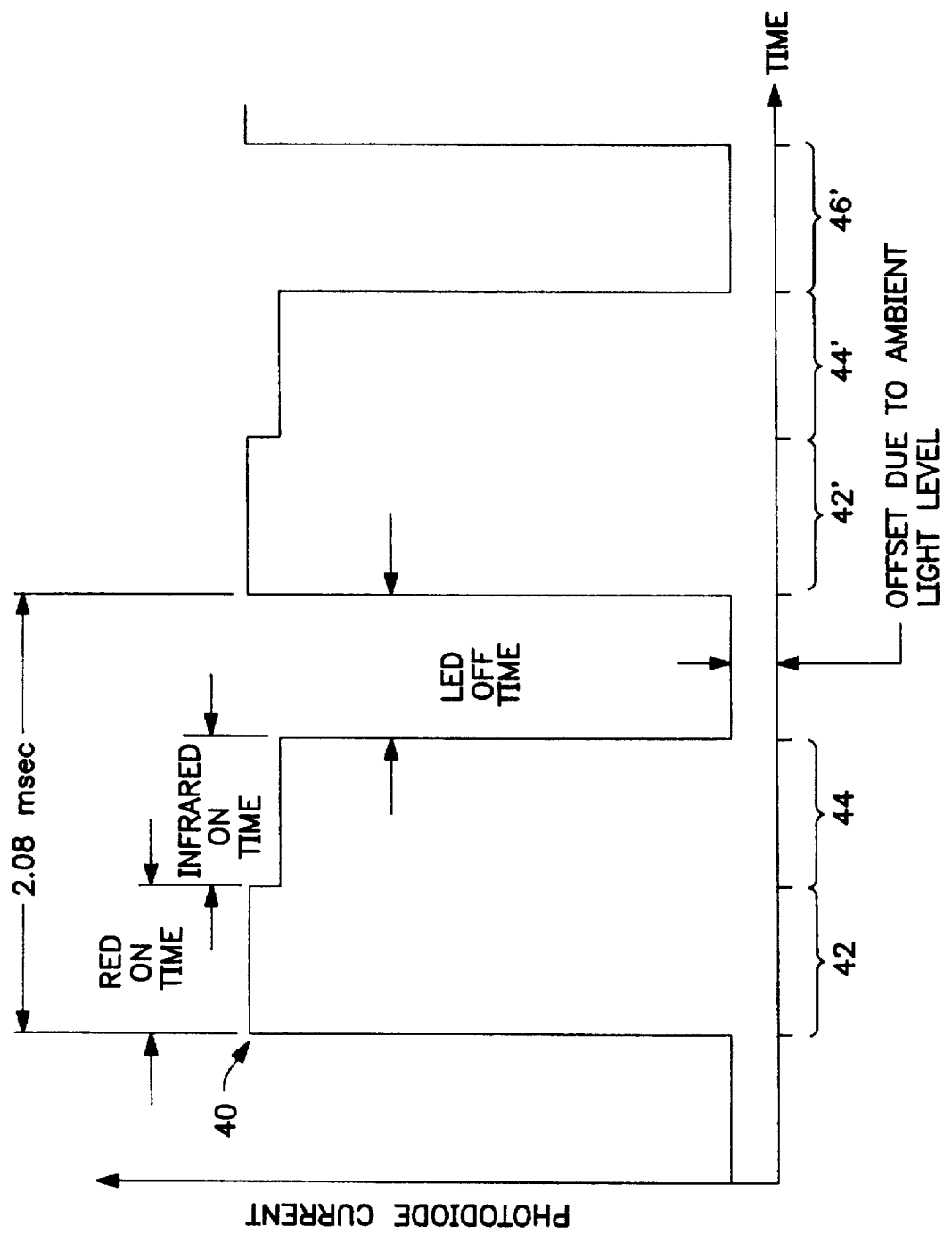
FIG. 4 is a schematic diagram of the transmitted-light detector output current from the sensor of FIG. 2 as a function of time.

Turning now to FIG. 3, a representative transmitted-intensity signal 30, denoted $I_\lambda(t)$, is shown as a function of time. The transmitted-intensity signal 30 includes a time-varying component which corresponds to pressure variations in arterial blood caused by cardiac pulsing. In general, the minima 32 in the transmitted-intensity signal 30 correspond to maxima in the arterial blood pressure, since at the maxima of arterial blood pressure, the arterial vessels in the finger are distended to a maximum extent and consequently, a greater quantity of arterial blood is present in the optical path between the light-emitting-diodes 24, 25 and the silicon photodiode 28 of the photoplethysmographic sensor 20, which leads to a greater absorption of radiation. Conversely, at the pressure minima of arterial blood, the arterial vessels are least distended, so that the quantity of arterial blood in the vessels is at a minimum, which corresponds to the maxima 34 of the transmitted-intensity signal 30 shown in FIG. 3.

The preferred photoplethysmographic perfusion index monitor samples the transmitted-intensity signal 30 shown in FIG. 3 at a sequence of discrete times $\{t_j\}$. The sampling times $t_j$ are equally spaced by approximately 1/30th of a second, or about 33.3 msec.

As may be seen in the scale-expanded inset in FIG. 3, the transmitted-intensity signal 30 changes by an increment $\Delta I(t_j)$ over a time interval defined by the successive sampling times $t_{j-1}, t_j$. Specifically, the incremental change in transmitted intensity is given by:

$$\Delta I(t_j) = [I_{\lambda 1}(t_j) - I_{\lambda 1}(t_{j-1})]$$

A transmitted-intensity signal base value $I(t_{[j-1,j]})$ is defined with respect to the sampling interval $t_{j-1}, t_j$ as shown in FIG. 3. The transmitted-intensity signal base value is preferably given by the equal-weighted average $[I(t_j)+I(t_{j-1})]/2$.

Light emitting diodes 24, 25 are driven in a time division multiplexed fashion and the detector 28 signal is synchronously demodulated to allow the monitor electronics to differentiate between the transmitted light received from one channel verses the other. The light source may be any approximately monochromatic light source including but not limited to LEDs, laser diodes, or filtered white light.

The red and infra-red light transmitted-intensity signals are digitally sampled simultaneously at sampling-time intervals of about 33 milliseconds. A sequence of sampled data points 50 from a representative red-light transmitted-intensity signal and a corresponding sequence 52 from a representative infrared-light transmitted-intensity signal are shown in FIG. 5 as a function of time.

Figure 5:
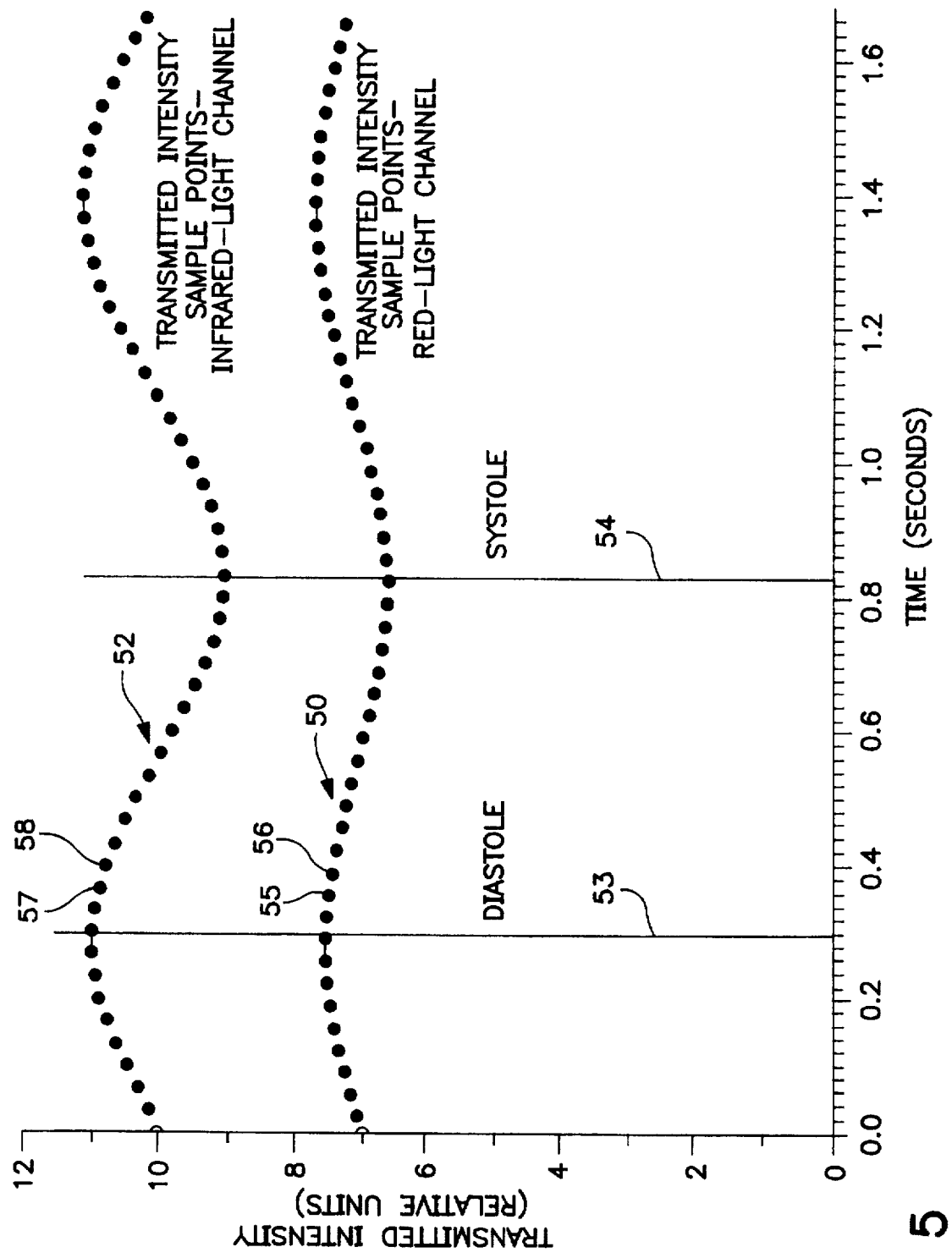
FIG. 5 is a graph showing the sampled transmitted intensity signals from the sensor of FIG. 2 for the infrared and red center wavelengths, respectively.

For the sequence of red-light transmitted-intensity-signal data points 50 illustrated in FIG. 5, the sample times $t_j$ corresponding to the data points may be indexed sequentially beginning with a sample time $t_o$ at the time indicated by diastole 53. Consequently, a pair 25 of successive data points 55, 56 from the sequence of red-light transmitted-intensity-signal data points 50 may be denoted $I_{\lambda 1}(t_2)$ and $I_{\lambda 1}(t_3)$ respectively corresponding to sampling times $t_2$ and $t_3$. The pair 55, 56 of successive data points $I_{\lambda 1}(t_2)$ and $I_{\lambda 1}(t3)$ may be used to calculate a red-wavelength incremental transmitted-intensity ratio corresponding to the sampling time $t_3$ as follows:

$$\frac{\Delta I_{\lambda_1}(t_3)}{I_{\lambda_1}(t_3)} = \frac{I_{\lambda_1}(t_3) - I_{\lambda_1}(t_2)}{[I_{\lambda_1}(t_3) + I_{\lambda_1}(t_2)]/2} .$$

Similarly for the infrared wavelength $$\frac{\Delta I_{\lambda_2}(t_3)}{I_{\lambda_2}(t_3)} = \frac{I_{\lambda_2}(t_3) - I_{\lambda_2}(t_2)}{[I_{\lambda_2}(t_3) - I_{\lambda_2}(t_2)]/2} .$$

From extinction coefficients $E_{\lambda 1}{}^O$, $E_{\lambda 1}{}^R$, $E_{\lambda 2}{}^O$, and $E_{\lambda 2}{}^O$ shown in the curves of oxygenated and reduced hemoglobin of FIG. 1, and the red- and infrared-channel incremental transmitted-intensity ratios corresponding to the sampling time $t_3$ determined above, a path length change $\Delta L(t_3)$ corresponding to the sampling time $t_3$ may be determined as follows:

$$\Delta L(t_3) = \frac{1}{[H_b](E^O_{\lambda_1} E^R_{\lambda_2} - E^O_{\lambda_2} E^R_{\lambda_1})}$$

$$\left[ (E^R_{\lambda_2} - E^O_{\lambda_2}) \frac{\Delta I_{\lambda_1}(t_3)}{I_{\lambda_1}(t_3)} - (E^R_{\lambda_1} - E^O_{\lambda_1}) \frac{\Delta I_{\lambda_2}(t_3)}{I_{\lambda_2}(t_3)} \right]$$

Summing the sequence of path length change values $\Delta L(t_j)$ corresponding to the succession of sampling times from $t_o$ to $tl_6$, which spans the time from diastole 53 to systole 54 indicated on FIG. 5. Thus $$PI = \left| \sum_{\text{Diastole}}^{\text{Systole}} \Delta L(t_j) \right| .$$

The exact extinction coefficients used in the system are selected to correspond to the spectral content of the light sources in the particular sensor in use. This means that different extinction coefficients may be used with different sensors.

Figure 6:
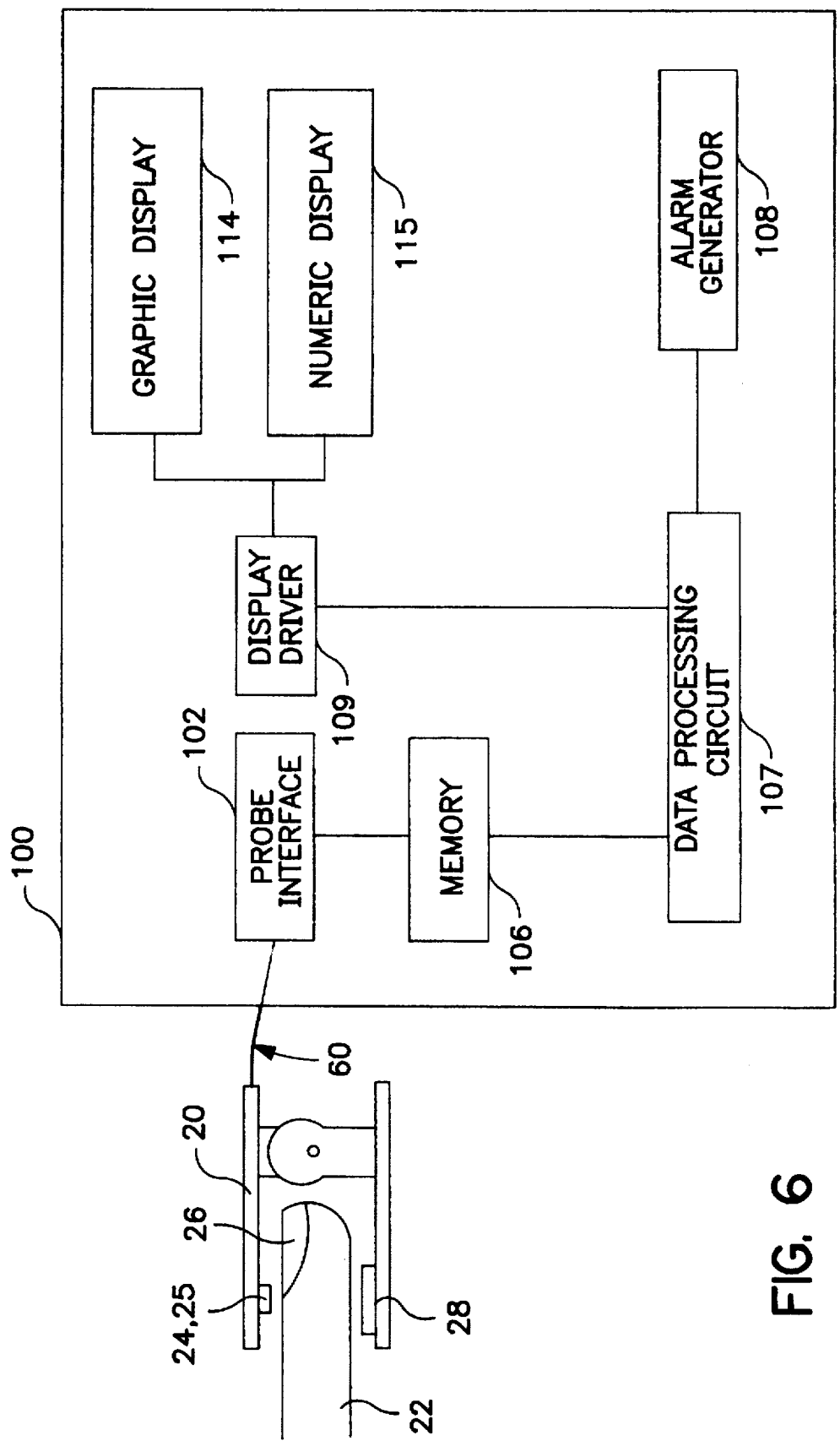
FIG. 6 is a diagram showing an embodiment of the apparatus of the claimed invention.

FIG. 6 depicts a preferred embodiment of a photoplethysmographic apparatus for implementing the present invention. Sensor 20 includes emitters 24, 25 each emit light having a spectral content defined by a center wavelength. Red light emitter 24 emits light with a center wavelength in the red band of the spectrum and infrared light emitter 25 emits light with a center wavelength in the infrared band. The light of each emitter 24, 25 is directed into the finer tip 22 near the base of the finger nail 26. The intensity of the light transmitted through finger tip 22 is detected by silicon photodetector 28 also part of sensor 20. The transmitted light intensity signal generated by photodetector 28 is transmitted via cable 60 to the monitor 100 via probe interface 102. Probe interface 102 typically converts the analog transmitted light intensity signal into a set of digital measurements via a well-known analog-to-digital converter. The digitized transmitted light intensity signal is then stored in memory 106 for processing by the data processing circuit 107. The data processing circuit 107 executes the instructions, also stored in memory 106, that are necessary to determine the perfusion index from the raw data, i.e., the digitized transmitted light intensity signal received from photodetector 28. Upon calculation of the perfusion index in accordance with the disclosed algorithms the perfusion index is transmitted to display driver 109 for display in the graphic display 114 and/or numeric display 115 which can consist of LCD, CRT, plasma or other appropriate displays. An alarm could also be generated via alarm generator 108 if the perfusion index falls below a predetermined range.

Memory 106 may also store a table of the effective extinction coefficients for emitters 24, 25 having spectral contents characterized by a variety of center wavelengths. Information on the center wavelength of the actual emitter being used may be encoded by a variety of known means, including bin resistors, diodes and connector pin encoding. This information can then be used by the data processing circuit 107 in order to select the proper extinction coefficients from the stored table for each of the emitters being used in the apparatus. In such a way, spectral content compensation can be accomplished in instances where a variety of sensors 20 each containing emitters with somewhat differing center wavelengths are used with one monitor 100.

Although the above description is of a preferred embodiment of the present invention it is expected that those skilled in the art can and will design alternate embodiments of this invention which fall within the scope of the claims set forth herein.

We claim:

1. A method for generating a perfusion index for a patient wherein a portion of tissue of the patient is perfused by pulsating arterial blood, the method comprising the steps of:
    a. generating from at least one emitter at least one approximately monochromatic light signal having a unique spectral content;
    b. directing each of the, at least one, approximately monochromatic light signals into the portion of tissue;
    c. detecting light transmitted through the portion of tissue to generate a received light intensity signal responsive to the detected light for each of the approximately monochromatic light signals;
    d. determining from the received light intensity signals generated for each of the approximately monochromatic light signals an optical path length change for each of a plurality of sampling time intervals; and,
    e. summing a plurality of the optical path length changes over a predetermined total time interval to generate the perfusion index value.

2. The method for generating a perfusion index according to claim 1 wherein the predetermined total time interval is the time interval for a systolic to diastolic transition.

3. The method for generating a perfusion index according to claim 1 wherein the predetermined total time interval is the time interval for a diastolic to systolic transition.

4. The method according to claim 1 wherein the predetermined total time interval is the time interval for contiguous diastolic to systolic and systolic to diastolic transitions.

5. The method according to claim 1 wherein the predetermined total time interval is the time interval for contiguous systolic to diastolic and diastolic to systolic transitions.

6. The method for measuring perfusion according to claim 1 wherein the predetermined total time interval includes at least one complete half-cardiac cycle having a peak and a valley.

7. The method according to claim 6 wherein the summing of the plurality of optical path length changes occurs from the peak to the valley of one complete half-cardiac cycle.

8. The method according to claim 6 wherein the summing of the plurality of optical path length changes occurs from the valley to the peak of one complete half-cardiac cycle.

9. The method for generating a perfusion index according to claim 1 in which the spectral content of a first emitter is characterized by a center wavelength of approximately 660 nm and the spectral content of a second emitter is characterized by a center wavelength of approximately 940 nm.

10. The method of generating a perfusion index according to claim 1 in which the emitter is characterized by a center wavelength of approximately an isobestic wavelength between 750 nm and 850 nm.

11. The method of generating a perfusion index according to claim 1 further comprising the steps of:
    selecting an extinction coefficient related to the spectral content of each of the emitters in use; and,
    calculating the perfusion index based on the selected extinction coefficients.

12. The method for measuring perfusion according to claim 1, further comprising the steps of:
    (f) repeating steps (a) through (e) in claim 1 a plurality of times to obtain a sequence of perfusion index values; and
    (g) averaging the perfusion index values obtained in step (f) above to obtain an average perfusion index value.

13. The method of generating a perfusion index according to claim 1 further comprising the step of displaying the perfusion index value to a user.

14. The method of generating an average perfusion index value according to claim 12 further comprising the step of displaying the average perfusion index value to a user.

15. An apparatus for generating a perfusion index indicative of the perfusion of a portion of tissue of a patient by pulsating arterial blood comprising a probe and a monitor;
    the probe further comprising:
        emitting means for illuminating the tissue portion of the patient with one or more approximately monochromatic light signal each having a unique spectral content;
        means for detecting the light transmitted through the tissue portion;
        means for generating a received light intensity signal responsive to the detected light for each of the one or more approximately monochromatic light signals;
        means for transmitting the received light intensity signals to the monitor; and,
    the monitor further comprising:
        calculating means for determining, from the received light intensity signals generated for each of the approximately monochromatic received light signals, an optical path length change for each of a plurality of sampling time intervals thereby generating a plurality of optical path length changes; and,
        means for summing the plurality of optical path length changes over a predetermined total time interval to generate the perfusion index.

16. The apparatus for generation of a perfusion index according to claim 15 wherein the emitting means emits one approximately monochromatic light signal having a spectral content characterized by a center wavelength approximately at an isobestic wavelength between 750 nm and 850 nm.

17. The apparatus for generation of a perfusion index according to claim 15 wherein the emitting means emits at least two approximately monochromatic light signals having spectral contents with center wavelengths at approximately 660 nm and 940 nm.

18. The apparatus for generation of a perfusion index according to claim 15 wherein the means for summing the plurality of optical length path changes sums the plurality of optical length path changes for a time interval equivalent to a transition from systolic to diastolic.

19. The apparatus for generation of a perfusion index according to claim 15 wherein the means for summing the plurality of optical length path changes sums the plurality of optical length path changes for a time interval equivalent to a transition from diastolic to systolic.

20. The apparatus for generation of a perfusion index according to claim 15 wherein the means for summing the plurality of optical length path changes sums the plurality of optical length path changes for a time interval containing at least one half cardiac cycle having a peak and a valley.

21. The apparatus for generation of a perfusion index according to claim 20 wherein the means for summing the plurality of optical path length changes sums the plurality of optical length path changes from the peak to the valley of the half cardiac cycle.

22. The apparatus for generation of a perfusion index according to claim 15 wherein the monitor further comprises a means for displaying the perfusion index.

23. The apparatus for generation of a perfusion index according to claim 15 wherein the monitor further comprises a means for calculating an average perfusion index value.

* * * * *